(12) United States Patent
O'Lenick

(10) Patent No.: US 8,168,817 B1
(45) Date of Patent: May 1, 2012

(54) CITRIC ACID ESTERS

(75) Inventor: Kevin A. O'Lenick, Dacula, GA (US)

(73) Assignee: SurfaTech Corp, Lawrenceville, GA (US)

( * ) Notice: Subject to any disclaimer, the term of this patent is extended or adjusted under 35 U.S.C. 154(b) by 9 days.

(21) Appl. No.: 12/927,662

(22) Filed: Nov. 8, 2010

(51) Int. Cl.
*C07C 69/34* (2006.01)
(52) U.S. Cl. ...................................................... 560/190
(58) Field of Classification Search .................. None
See application file for complete search history.

(56) References Cited

U.S. PATENT DOCUMENTS

| 4,868,236 | A | | 9/1989 | O'Lenick | |
|---|---|---|---|---|---|
| 5,786,389 | A | * | 7/1998 | O'Lenick et al. | 514/552 |
| 6,589,519 | B1 | * | 7/2003 | Restle et al. | 424/70.12 |

OTHER PUBLICATIONS

Database Caplus Chemical Abstracts Service, Columbus, Ohio, US; Database Accession No. 2010:199537, Abstract of FR 2934157.: "Cosmetic composition containing particulate cationic surface-active agent, a fatty alcohol, and a fatty ester, use, and process".*

* cited by examiner

*Primary Examiner* — Karl J Puttlitz

(57) ABSTRACT

The present invention relates to the ability of certain unsaturated Guerbet esters to repair damage to the hair and skin. The compounds are oleate esters of Guerbet alcohols. The low viscosity, polarity of the ester group and very low titer point allow the esters of the present invention to spread rapidly and efficiently on the hair and skin, providing an elegant feel and lubricate the surface of the hair or skin repairing damage done to the hair or skin by washing, and allowing for the replacement of the oils from inside the hair or skin.

11 Claims, No Drawings

CITRIC ACID ESTERS

GOVERNMENT SPONSORSHIP

None

FIELD OF THE INVENTION

The current invention is drawn to a series of citrate esters having high melting domains and liquid domains at room temperature. This that results in an ability to alter hardness, melt point and skin feel, making outstanding waterproofing and emollient properties when applied to skin.

The compositions of the present invention are oil soluble esters that are modified to have unique skin spreadability properties. This provides particular value in the personal care arena. Specifically, the esters are useful as a carrier in antiperspirants, pigmented products, skin care products, and the like since they spread rapidly and efficiently on the skin from a stiff gel providing emmoliency and a host of ester soluble additives including sun screen actives, hydroxy acids, antioxidants, flavonoids, tocopherol, vitamins and the like. They can be formulated into products to provide an appealing feel on the skin and provide a lubricious property which improve the properties of skin creams, skin care lotions, moisturizers, facial treatments such as acne or wrinkle removers, personal and facial cleansers, liquid soaps, bath oils, perfumes, colognes, sachets, sunscreens, pre-shave and after-shave lotions, shaving soaps, and shaving lathers. It can be used in hair shampoos, hair conditioners, hair sprays, mousses, permanents, depilatories, and cuticle coats, to enhance cosmetic elegance.

Citric acid is a common material of natural origin. The structure is:

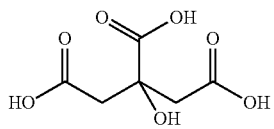

CAS Registry Number: 77-92-9
CA Index Name: 1,2,3-Propanetricarboxylic acid, 2-hydroxy- Citric acid is made by fermentation, using cultures of *Aspergillus niger* are fed on a sucrose or glucose-containing medium.

Citric acid is one of a series of compounds involved in the physiological oxidation of fats, proteins, and carbohydrates to carbon dioxide and water. This series of chemical reactions is central to nearly all metabolic reactions, and is the source of two-thirds of the food-derived energy in higher organisms. Krebs received the 1953 Nobel Prize in Physiology or Medicine for the discovery. The series of reactions is known by various names, including the citric acid cycle, the Krebs cycle, and the tricarboxylic acid cycle Citrate esters are known. They conform to the following structure:

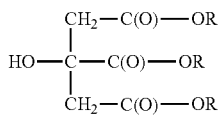

The esters are made by the reaction of fatty alcohols with citric acid.

U.S. Pat. No. 4,292,192 issued to Hooper, et al. teaches that Detergent bars for personal washing are given a deodorant property by including an ester of citric acid. The ester may be an acetyl derivative. The amount of ester used will be in the range of from about 0.3% to about 3%. Examples of the esters are triethyl citrate and acetyl tributyl citrate.

U.S. Pat. No. 2,122,716 describes long chain esters of citric acid, e.g., tridodecyl citrate, which have been used as plasticizers for resinous compositions.

U.S. Pat. Nos. 3,239,555 and 3,241,992 disclose bis-citric acid esters made by esterifying the acid groups with C1 to C18 alcohols and coupling the esters with dibasic acids. Such esters are useful as plasticizers for plastics.

U.S. Pat. No. 3,251,792, the acid groups of citric acid are esterified with alkyl, aryl, cycloalkyl and haloaryl alcohols and the hydroxyl group is esterified with a carbonyl compound. Such compounds are used as stabilizers for polypropylene.

U.S. Pat. No. 5,089,658 issued Feb. 18, 1992 to Elmore et al, is directed to citric acid esters. In one aspect, this invention pertains to citric acid esters, which contain at least one primary or secondary hydroxyl group. In another aspect, this invention relates to citric acid esters, which are reactive diluents. In still another aspect, this invention pertains to citric esters, which are pigment dispersants. The citric ester compositions of this invention are useful as reactive diluents for high solids thermosetting coating composition and as pigment dispersants for use in thermosetting coatings.

U.S. Pat. No. 4,868,236 to O'Lenick discloses a guerbet citric ester and polymers thereof useful in plastic lubrication.

None of these patents provide polyester derivatives of mixed fatty esters of citrate as envisioned by the present invention.

THE INVENTION

Objectives of the Invention

The object of present invention is to provide a an ester specific solid ester that can be altered from a hard solid to a soft lubricious liquid.

The method of doing this is to provide a molecule with liquid domains and solid domains present in the same triester. The solid domain is provided by a high molecular weight fatty alcohol and the liquid provided by a branched alcohol, specifically a unsaturated alcohol, a iso-alcohol or preferably oleyl alcohol.

Another objective of the present invention is a process for providing emolliency to the skin by applying the compositions of the present invention, The invention is also directed to application of sunscreen actives, hydroxy acids, antioxidants, flavonoids, tocopherol, vitamins and the like to the skin in gelled form.

Other objectives will become clear as one reads the disclosure.

All temperatures disclosed herein are degrees C, All percentages are percentages by weight.

All patents referred to herein to the extent permitted are incorporated herein by reference.

SUMMARY OF THE INVENTION

The present invention is directed to a citrate ester that contains liquid portions and solid portions when the ester is cooled to ambient temperatures. The ratio of solid to liquid results in products that have very different properties. The properties that can be varied are hardness, melt point, waterproofing, spreadability and skin feel.

The higher the molecular weight of the solid alcohol, the better the waterproofing, the harder the ester and the less spreadable the ester. The higher the ratio of the liquid alcohol to solid alcohol the softer the ester, the more spreadable and the material less the waterproofing.

DETAILED DESCRIPTION OF THE INVENTION

The present invention is directed an ester conforming to

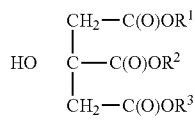

wherein:
$R^1$ $R^2$ and $R^3$ are independently a mixture of:
(a) alkyl having 30 to 60 carbon atoms;
an
(b) oleyl alcohol is cis-9-octadecen-1-ol and conforms to the following structure:

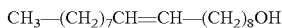

The esters of the current invention are made by a esterification of citric acid with a mixture of two type of alcohols wherein one type is alkyl having 30 to 50 carbon atoms and the other type is oleyl alcohol.

The products of the present invention are made by the esterification reaction of:
(a) citric acid conforming to the following structure:

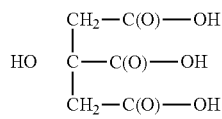

(b) oleyl alcohol conforming to the following structure:

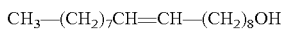

and
(c) a fatty alcohol conforming to the following structure;

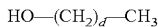

d is an integer ranging from 29 to 59.

Another aspect of the present invention is a process for conditioning hair and skin which comprises contacting the hair or skin with an effective conditioning concentration of a polyester made by the esterification reaction of:
(a) citric acid conforming to the following structure:

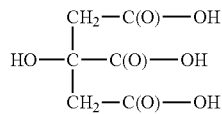

(b) oleyl alcohol conforming to the following structure:

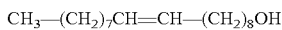

resulting in liquid high molecular weight domains (d) a fatty alcohol that is solid at room temperature

d is an integer ranging from 29-59 (resulting in solid domains).

Where there are two different types of ester group present, one liquid and one solid, the resulting structure cannot crystallize completely, since the liquid domains in the polymer act as molecular crystal distorters, resulting in a polymer that although having the same melting point, flows more easily when pressure is applied. The resulting solid will be soft and flowable, rather than hard and un-yielding.

Preferred Embodiment

In a preferred embodiment d is 29.
In a preferred embodiment d is 38.
In a preferred embodiment d is 46.
In a preferred embodiment d is 59
In a preferred embodiment said effective conditioning concentration ranges from 0.1 to 20% by weight.
In a preferred embodiment the ratio of oleyl alcohol to fatty alcohol ranges from 0.1:1 to 1:.0.1 by weight.
In a preferred embodiment the ratio of oleyl alcohol to fatty alcohol ranges from 0.2:1 to 1:.0.2 by weight Raw Materials
Citric Acid Citrate is an item of commerce commercially available from a variety of sources including Pfizer. It conforms to the following structure:

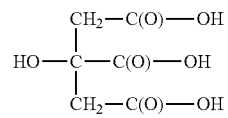

Oleyl Alcohol

Oleyl alcohol is an item of commerce sold by Cognis and JarChem. Oleyl alcohol conforming to the following structure:

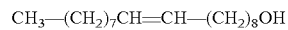

CAS Number 143-28-2
EINECS Number 205-597-3

Fatty Alcohols

Examples 1-4

The alcohols useful in making the esters of the present invention conform to the following structure:

wherein
R is alkyl having 30 to 60 carbon atoms;
In a preferred embodiment the alcohols are UNILIN™ alcohols. Unilin is a trademark of UNILIN is a trademark of Baker Hughes Incorporated.

Baker Hughes defines the alcohols as "based on proprietary technology, UNILIN™ Alcohols are fully saturated, long chain, linear primary alcohols. Compared to other commercially available synthetic alcohols, UNILIN Alcohols are of higher molecular weight, greater crystallinity, and higher purity with an 80% primary alcohol concentration."

Baker Hughes continues "Linear alcohols are traditionally limited to C30 and lower, while UNILIN Alcohols are available with average carbon chain lengths up to C50. A further attractive feature of the UNILIN Alcohols is the relatively narrow 1.1 polydispersity (Mw/Mn)."

| Example | R Value* | Trade Name | OH Value | Molecular Weight* | d value |
|---|---|---|---|---|---|
| 1 | C30H61 | Unilin 350 | 128.4 | 437 | 29 |
| 2 | C39H79 | Unilin 425 | 99.7 | 563 | 38 |
| 3 | C47H95 | Unilin 550 | 83.1 | 675 | 46 |
| 4 | C60H21 | Unilin 700 | 65.5 | 857 | 59 |

*Calculated (Molecular weight − 16)/14
*Measured.
**Calculated (56110/OH Value)

The molecular weight is calculated from the hydroxyl value and the R-value from the molecular weight. The Tradename is not given merely for reference.

Esterification Process
General Procedure

To a round bottom flask equipped with thermometer, agitation and nitrogen sparge is added the specified number of grams of alcohol (Example 1-4), and oleyl alcohol. The reaction mixture us heated to 160-170 C. Next the specified number of grams of citric is added under good agitation. Next add 0.1% by weight of all components of stannous oxylate. The temperature is increased to 170-190° C. for eight to twenty hours, water is generated and distilled off. The reaction is stopped when the water ceases to come off.

| | Citric Acid | Fatty Alcohol | | Oleyl alcohol |
|---|---|---|---|---|
| | Grams | Example | Grams | Grams |
| 5 | 20.4 | 1 | 14.3 | 65.3 |
| 6 | 25.0 | 1 | 34.1 | 41.0 |
| 7 | 18.7 | 1 | 6.8 | 74.5 |
| 8 | 33.3 | 1 | 66.8 | 3.0 |
| 9 | 13.7 | 2 | 42.3 | 44.0 |
| 10 | 11.6 | 2 | 69.5 | 18.9 |
| 11 | 15.2 | 2 | 24.5 | 60.4 |
| 12 | 10.2 | 2 | 89.8 | 3.0 |
| 13 | 12.7 | 3 | 46.8 | 40.6 |
| 14 | 10.1 | 3 | 73.2 | 16.6 |
| 15 | 14.5 | 3 | 27.9 | 57.6 |
| 16 | 8.6 | 3 | 91.5 | 3.0 |
| 17 | 11.2 | 4 | 52.7 | 36.0 |
| 18 | 8.5 | 4 | 77.6 | 17.0 |
| 19 | 13.4 | 4 | 33.0 | 53.6 |
| 20 | 7.0 | 4 | 93.0 | 3.0 |

The reaction is monitored by acid value, which becomes vanishingly low during the reaction. The products are used without purification.

Applications Examples

The compositions of the present invention range from rock hard to very soft liquids. The rock hard solids can be used to alter the melting pint of stick products like lipsticks. The soft solids are used in skin care where they are applied as emollient butters or waxes.

The higher the number of carbon atoms in the solid ester, the higher the melting point of the composition. At the melt point the structured gel dissolves making a liquid, upon cooling the structured gel reforms, making the technology very flexible.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. A cosmetic ester composition made by an esterification reaction of:

(a) citric acid conforming to the following structure:

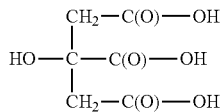

(b) oleyl alcohol conforming to the following structure:

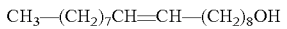

and (c) an alcohol that is solid at room temperature conforming to the following structure;

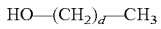

d is an integer ranging from 29 to 59.

2. A cosmetic ester composition of claim 1 wherein d is 29.
3. A cosmetic ester composition of claim 1 wherein d is 38.
4. A cosmetic ester composition of claim 1 wherein d is 46.
5. A cosmetic ester composition of claim 1 wherein d is 59.
6. A process for providing waterproofing and emollient properties to hair and skin which comprises contacting hair or skin of a subject with an effective concentration of a cosmetic ester composition of claim 1.
7. A process of claim 6 wherein said effective conditioning concentration ranges from 0.1 to 20% by weight.
8. A process of claim 6 wherein d is 29.
9. A process of claim 6 wherein d is 38.
10. A process of claim 6 wherein d is 46.
11. A process of claim 6 wherein d is 59.

* * * * *